United States Patent
Ehring

(10) Patent No.: US 10,274,428 B2
(45) Date of Patent: Apr. 30, 2019

(54) INTERGRATION OF FLUORESCENCE DETECTION CAPABILITY INTO LIGHT ABSORBANCE MEASUREMENT APPARATUS

(71) Applicant: GE HEALTHCARE BIO-SCIENCES AB, Uppsala (SE)

(72) Inventor: Hanno Ehring, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 15/528,123

(22) PCT Filed: Nov. 24, 2015

(86) PCT No.: PCT/EP2015/077567
§ 371 (c)(1),
(2) Date: May 19, 2017

(87) PCT Pub. No.: WO2016/083416
PCT Pub. Date: Jun. 2, 2016

(65) Prior Publication Data
US 2017/0356848 A1 Dec. 14, 2017

(30) Foreign Application Priority Data
Nov. 25, 2014 (SE) ...................... 1451419

(51) Int. Cl.
*G01N 21/64* (2006.01)
*G01N 21/05* (2006.01)
(Continued)

(52) U.S. Cl.
CPC .......... *G01N 21/645* (2013.01); *G01N 21/05* (2013.01); *G01J 3/42* (2013.01); *G01J 3/4406* (2013.01);
(Continued)

(58) Field of Classification Search
CPC ...... G01N 21/645; G01N 21/05; G01N 21/33; G01N 2021/421; G01N 2021/1736;
(Continued)

(56) References Cited

U.S. PATENT DOCUMENTS

| 4,867,559 A | 9/1989 | Bach |
| 2007/0048868 A1* | 3/2007 | Shibata .............. G01N 35/1016 436/43 |

(Continued)

FOREIGN PATENT DOCUMENTS

| EP | 0442025 A1 | 8/1991 |
| WO | 2014/088498 A1 | 6/2014 |

OTHER PUBLICATIONS

PCT International Search Report and Written Opinion for PCT Application No. PCT/EP2015/077567 dated Feb. 29, 2016 (13 pages).

*Primary Examiner* — Nicole M Ippolito
(74) *Attorney, Agent, or Firm* — Eversheds Sutherland (US) LLP

(57) ABSTRACT

Disclosed is apparatus (1) for measuring fluorescence and absorbance of a substance in a sample, said apparatus (1) comprising: a flow cell (2) for containing a sample, a first light source (3), a first conductor (5) for transmitting light from the first light source (3) to the flow cell (2) for irradiating a sample contained therein, a second conductor (7) for transmitting light from the flow cell (2) to a sample detector (9) arranged to detect an electromagnetic radiation that has passed through said cell (2), and a processing unit (16) arranged to receive a first signal (31) from a reference detector (15) and a second signal (32) from the sample detector (9) and to determine an absorbance based on said first and second signals (31,32), said apparatus (1) further comprising a second light source (4), a third conductor (6) for transmitting light from the second light source (4) to the (Continued)

cell (2) and wherein the sample detector (9) is further arranged to also detect fluorescence signals in the light that has passed through the flow cell (2). The invention also relates to a method for measuring the absorbance and the fluorescence of a substance in a sample.

23 Claims, 2 Drawing Sheets

(51) Int. Cl.
    *G01J 3/42*     (2006.01)
    *G01J 3/44*     (2006.01)
    *G01N 21/33*     (2006.01)
    *G01N 21/17*     (2006.01)

(52) U.S. Cl.
    CPC ........ *G01J 2003/421* (2013.01); *G01N 21/33* (2013.01); *G01N 2021/174* (2013.01); *G01N 2021/1736* (2013.01); *G01N 2021/1738* (2013.01); *G01N 2021/6482* (2013.01); *G01N 2021/6484* (2013.01); *G01N 2021/6491* (2013.01); *G01N 2201/0696* (2013.01)

(58) Field of Classification Search
    CPC ... G01N 2021/1738; G01N 2021/6482; G01N 2021/6484; G01N 2201/6491; G01N 2201/0696; G01J 3/42; G01J 3/4406
    USPC .............................. 850/21, 30, 31; 250/428
    See application file for complete search history.

(56) References Cited

U.S. PATENT DOCUMENTS

| | | |
|---|---|---|
| 2009/0046287 A1 | 2/2009 | Haught et al. |
| 2012/0194805 A1 | 8/2012 | Ness et al. |
| 2014/0095082 A1* | 4/2014 | Kuderer ................. G01N 30/78 702/22 |
| 2016/0061732 A1* | 3/2016 | Yamada ................. G01N 33/80 435/288.7 |

* cited by examiner

INTERGRATION OF FLUORESCENCE DETECTION CAPABILITY INTO LIGHT ABSORBANCE MEASUREMENT APPARATUS

CROSS REFERENCE TO RELATED APPLICATIONS

This application claims the priority benefit of PCT/EP2015/077567 filed on Nov. 24, 2015 which claims priority benefit of Swedish Application No. 1451419-4 filed Nov. 25, 2014. The entire contents of which are hereby incorporated by reference herein.

FIELD OF THE INVENTION

The present invention relates to an apparatus and a method for detecting the light absorbance and fluorescence of a substance in a sample.

BACKGROUND OF THE INVENTION

The accurate detection of various properties of a sample is an area with numerous applications in different fields of technology. Within liquid chromatography, for instance, the detection of fluorescence to determine the amount of a chemical element in a sample is often required. Fluorescence detection devices, however, are often expensive and bulky because they combine high sensitivity and wavelength selection capabilities. Often, a spectrometer is used to detect fluorescence signals of different wavelengths, as is known through CN2856989, for instance.

Other methods for measuring fluorescence are also known, for instance through the use of fiber-optical probes that are to be immersed in a sample and that are connected to a lower cost optical spectrometer. Thereby, a more cost efficient apparatus is achieved, but at a much lower sensitivity.

There is therefore generally a need for a method and apparatus for detecting fluorescence that can be produced in a cost efficient way and still maintain a high sensitivity and accuracy in measuring properties of a sample.

SUMMARY OF THE INVENTION

The object of the invention is to achieve a cost efficient apparatus and method for measuring the fluorescence and the light absorbance of a substance in a sample.

Herein, 'light' is intended to include visible and on visible electromagnetic radiation. Herein 'fluorescence' and similar words are intended to include light (visible or non visible) which is emitted by the substance (natural fluorescence), or light emitted by fluorescing molecules or other matter associated with the substance (induced fluorescence), for example fluorescence dyes attached to the substance. It will be understood that the term "substance" as used herein refers to any chemical entity. In particular, it includes organic compounds and inorganic compounds. Examples of organic compounds include, but are not limited to, proteins, peptides, carbohydrates, lipids, nucleic acids, protein nucleic acids, drug candidates and xenobiotics. Examples of inorganic compounds include metal salts, such as ferric sulphate, copper chloride, nickel nitrate, etc.

In a first aspect of the present invention, there is provided an apparatus and a method according to the appended independent claims, wherein a sample detector is arranged to detect absorbance and fluorescence of a substance in a sample. Thereby, the same apparatus can be used to measure both absorbance and fluorescence, giving the advantages of both a cost efficient high sensitivity fluorescence detection and the integration of these capabilities into an apparatus that is also arranged to measure another property of a sample, namely the absorbance. Since many components used for measuring fluorescence are also required for measuring absorbance, significant advantages can thereby be achieved.

According to an aspect of the invention, the sample detector is at least one photo detector. Thereby, the apparatus can be made small and cost efficient, and still allow for the detection of light of a number of different wavelengths.

According to one aspect of the invention, the first light source for measuring absorbance is an UV light emitting diode. Thereby, the advantages of a narrow bandwidth, low cost and stable component can be achieved, and having several other advantages including powering by battery or other low voltage power source and avoiding warm up time before the component can reliably be used.

According to one aspect of the invention, the second light source for measuring fluorescence is an UV light emitting diode. Thereby, a native fluorescence of the substance can be measured, without requiring the need to apply fluorescence molecules to the substance.

According to one aspect of the invention, at least one of the first light source and the second light source are pulsed. Thereby, the light sources can be controlled so that only one at a time emits light, giving the opportunity for measuring absorbance and fluorescence with a higher sensitivity and also allowing for a measuring of background light as a reference value without requiring either of the light sources to be switched off completely.

According to one aspect of the invention, a first filter is arranged between the second conductor and the sample detector, said first filter being arranged to block light of the wavelength emitted by the second light source. Thereby, the detection of fluorescence signals can be improved since a smaller amount of light irrelevant for the detection is allowed to reach the sample detector.

According to one aspect of the invention, the first conductor is also the third conductor so that light from the first light source and the second light source are transmitted through the same conductor to the cell. Thereby, the apparatus can be made with fewer components to further minimize the cost.

According to one aspect of the invention, the second conductor is arranged at an angle to the third conductor. Thereby, the amount of light from the second light source that is transmitted through the outlet and to the sample detector is decreased, improving the detection of fluorescence signals from the sample. Preferably, said angle is 90°, to minimize the amount of light from the second light source that is transmitted through the second conductor.

According to one aspect of the invention, the first inlet comprises a shutter element for preventing light from emitting from said first inlet. Thereby, light from the first light source can be prevented from irradiating the sample during fluorescence measuring if the light sources are not pulsed, thereby improving the detection of fluorescence signals.

According to one aspect of the invention, the second light source and the first filter are arranged to be replaceable by a user of the apparatus. Thereby, the user can select the light source and filter most suited to each specific application, without requiring further modifications to the apparatus and rendering the apparatus more versatile, while at the same time maintaining cost efficiency.

Further advantages and benefits of the present invention will be readily apparent to the person skilled in the art in view of the detailed description below.

BRIEF DESCRIPTION OF THE FIGURES

The invention will now be described in more detail with reference to the appended drawings, wherein.

DETAILED DESCRIPTION OF THE INVENTION

Figure 1:
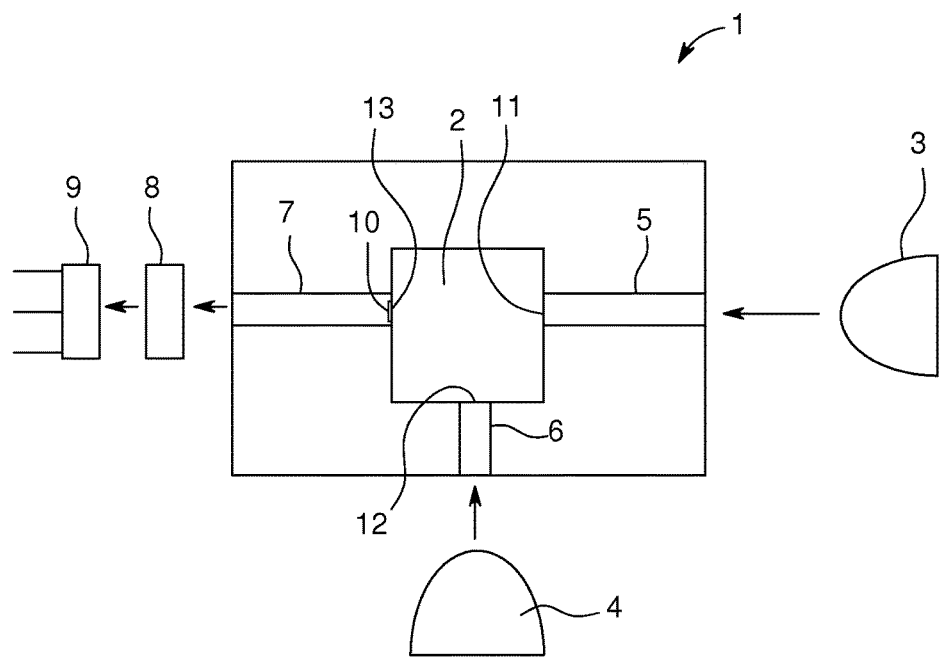
FIG. 1 is a schematic view disclosing a first embodiment of an apparatus according to the invention for measuring the fluorescence and the absorbance of a substance in a sample.

FIG. 1 is a schematic representation of a first preferred embodiment of an apparatus 1 according to the invention. The apparatus 1 comprises a first light source 3, preferably a UV LED that emits light suitable for use in measuring the absorbance of a sample placed in a flow cell 2 of the apparatus 1, as will be described in detail below with reference to FIG. 3. The light from the first light source 3 propagates toward the flow cell 2 through a first light path, in this case a light conductor in the form of a optical fiber 5, which is connected to the flow cell 2 at a first inlet 11. For the absorbance measurements, further components in the form of a beam splitter 14 and a reference detector 15 are generally required (see FIG. 3). It would, however, be possible to measure the absorbance without these components, for instance by using a reference sample such as water in the flow cell for obtaining a reference value. It is to be noted that the first light source 3 can alternatively be another type of light source that provides light of a different wavelength outside the UV range such as another type of LED for instance, if this is suitable for measuring absorbance of a sample. Light from the flow cell 2 is allowed to exit the flow cell 2 through an outlet 13 connected to a second light path in the form of an optical fiber light conductor 7, which transmits the light to a sample detector 9 through a first filter 8.

A second light source 4, preferably also a UV LED, is also arranged to irradiate the flow cell 2 and emits light that is suitable for measuring the fluorescence of a sample placed in the flow cell 2. The light from the second light source 4 propagates in use toward the flow cell 2 through a third light path in the form of an optical fiber light conductor 6, and enters the flow cell 2 through a second inlet 12.

The first filter 8 is preferably at least one optical band pass filter that is configured to block light of the wavelength emitted by the second light source 4 but allow light from the first light source 3 and light within an expected range for fluorescence signals to pass to improve the measuring of the fluorescence signals of the sample in the flow cell 2. Thus, light of a plurality of wavelength ranges can be allowed to pass the at least one optical filter. It is to be noted that additional band pass filters may also be placed adjacent to the first and second light sources 3, 4 as is well known in the art to allow only a narrow wavelength range, for instance 10 nm, to pass. It is advantageous to use a UV LED as the second light source, since this gives the opportunity to measure native fluorescence in the wavelength range of 280-300 nm for substances such as proteins, for instance. However, other kinds of light sources, such as other types of LED, for instance, may also be used if desired.

At the outlet 13, a shutter element 10 may also be arranged to block the light, as will also be described further below with reference to an embodiment where the second light source 4 is arranged adjacent to the first light source 3 and the fluorescence signals are allowed to exit the apparatus 1 through the third conductor 6.

Figure 2:
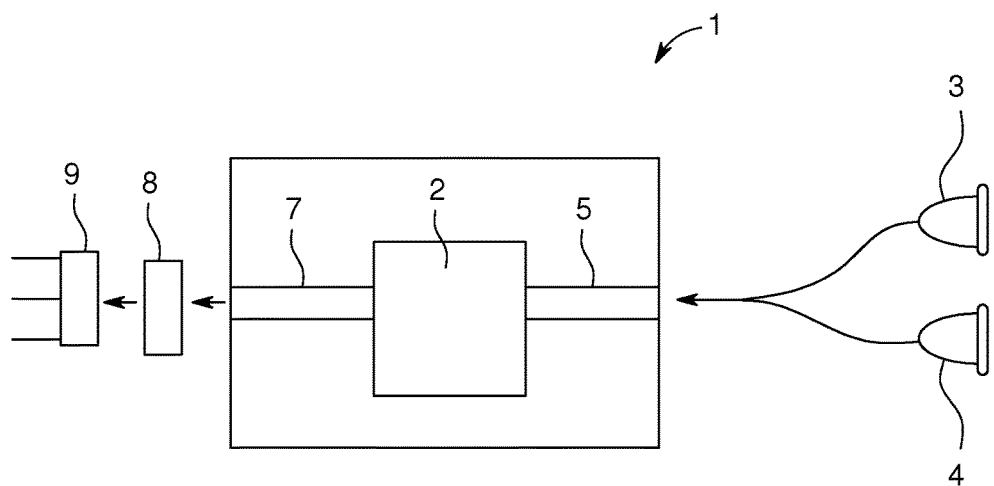
FIG. 2 is a schematic view of a second embodiment according to the invention.

FIG. 2 discloses a second embodiment of the apparatus according to the invention, differing from the first embodiment by using the first conductor 5 to transmit light both from the first light source 3 and from the second light source 4 to the flow cell 2. Thus, in this embodiment, the light from both sources enter the flow cell from the same direction. This is cost efficient since fewer components are required for the apparatus 1, and the light from both light sources 3, 4 can be transmitted through the same optical fiber. In order to still perform accurate fluorescence measurements with high sensitivity, the first filter 8 is arranged to block the wavelength of light emitted by the second light source 4. It is advantageous if the wavelengths of the first light source 3 and the second light source 4 differ enough to allow the light from the first light source 3 to pass the first filter 8 while at the same time blocking the light from the second light source 4.

It is to be noted that a single light source can alternatively be used instead of the first light source 3 and the second light source 4, provided that the fluorescence that is to be measured requires an excitation wavelength that is close to or identical to the wavelength required for measuring the absorbance of the sample. In the event that only one light source is used, the first filter 8 would of course need to be bypassed or omitted for the measuring of the absorbance. Alternatively, the first light source 3 and the second light source 4 can be mounted together within the same cover.

The sample detector 9, as has been mentioned above, is preferably at least one photo detector that is arranged to detect and measure the amplitude of light. The photo detector can for instance be a photo diode, an avalanche photo diode, a photomultiplier or a silicon photomultiplier. Compared to the use of a spectrometer for this application, the photo detectors mentioned above have the advantage of being small and cost efficient. This allows for easy handling and convenient use in different locations. In one embodiment, the sample detector 9 could also be arranged to be removable by the user, so that a photo diode capable of detecting certain wavelengths can be replaced with a photo diode capable of detecting other wavelengths. In one embodiment, the sample detector comprises a plurality of photo diodes, such as an array of photo diodes, thereby increasing the number of wavelengths that can be detected while still adding to the cost of the apparatus only marginally.

If desired, a number of light sources can be mounted side by side and the light from each source be transported together in the same optical fiber or fiber bundle, to be separated again at the flow cell 2 or at a number of different flow cells 2 containing different samples. In this multiplex embodiment, a plurality of light sources, each corresponding for instance to different fluorescence colors, can be used for irradiating the sample in the flow cell 2, and the amount of light of each color emitted as fluorescence signals can be detected, for instance by an array of photo diodes arranged to detect each color. In this event, each of the photo diodes would require a filter adapted for the photo diode itself, to prevent undesired light from reaching the diode. Alternatively, a single component providing wavelength demultiplexing and detection and comprising both diode and optical filters can be used as the sample detector 9, such as for instance an OptoFlash optical engine (trademark of the Newport Corporation).

Figure 3:
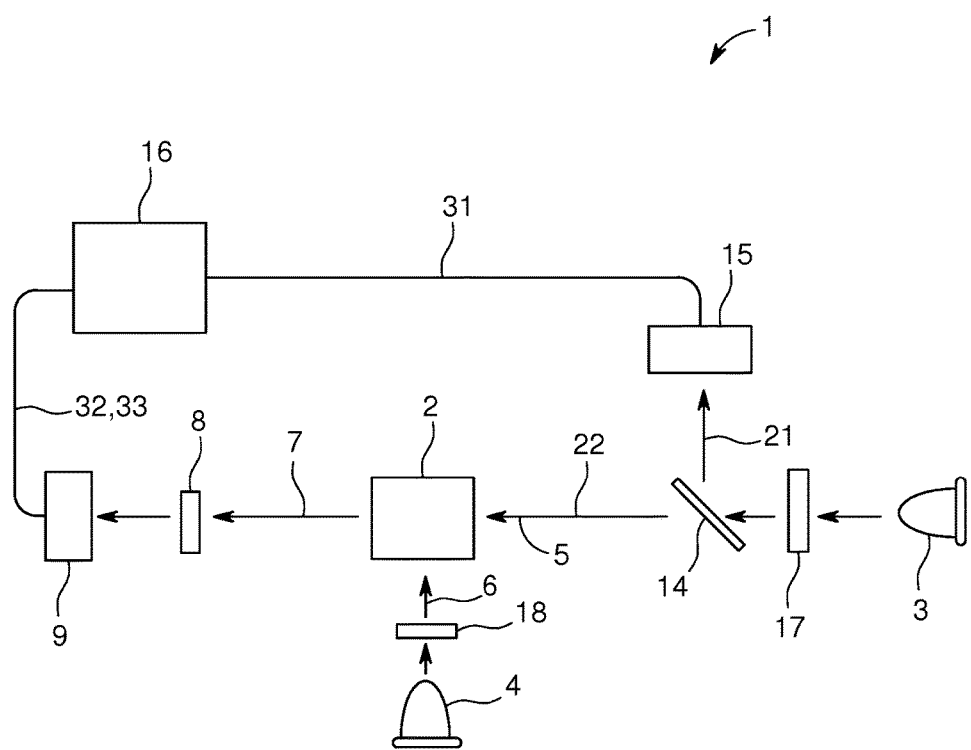
FIG. 3 is a schematic view of the first embodiment disclosing additional components of the invention.

FIG. 3 shows the apparatus 1 of FIG. 1 in more detail. The first light source 3 emits light suitable for measuring the absorbance of a sample, preferably light in the UV range in the case of measuring absorbance of a protein in the sample. The light may pass through a first additional band pass filter 17, which serves to filter the light and allow only a narrow wavelength range, preferably only about 10 nm or less, to pass. The light is then split into a first and a second portion 22 by a beam splitter 14, and the first portion 21 is transmitted to a reference detector 15 that detects electromagnetic radiation in the first portion 21 of light. The reference detector 15 can be a photo detector of the same type as the sample detector 9 suitable for detecting light at the wavelength emitted by the first light source 3. The reference detector 15 is further operatively connected to a processing unit 16 that is arranged to receive a first signal 31 corresponding to the amount of light being received by reference detector 15.

The second portion 22 of light is transmitted from the beam splitter 14 to the flow cell 2 through the first conductor 5 and enters the flow cell 2 through the first inlet 11 to irradiate the flow cell 2 and a sample contained therein. Some of the light is absorbed by the sample, and the remainder passes through to the outlet 13 and the second conductor 7 towards the sample detector 9. Before reaching the sample detector 9, the light passes through the first filter 8.

The sample detector 9, preferably in the form of at least one photo detector adapted for detecting light of the wavelength emitted by the first light source 3, thus receives what is left of the second portion 22 of light after passing through the flow cell 2 and detects the electromagnetic radiation of said light. A second signal 32 corresponding to the amount of light being received by the sample detector 9 is transmitted to the processing unit 16, to which the sample detector 9 is operatively connected.

By comparing the first signal 31, corresponding to the first portion 21 of light from the first light source 3, and the second signal 32, corresponding to the light that has passed through the flow cell 2 without being absorbed by the sample, the processing unit is arranged to determine the absorbance of the sample, as is well known in the art.

For the measuring of the fluorescence of the sample, the second light source 4, preferably also an UV LED, is arranged to emit light corresponding to a wavelength suitable for generating fluorescence signals in the sample. Thanks to the use of the UV LED emitting light with a wavelength of 260-300 nm, native fluorescence can be detected in various proteins or antibodies. For the detection of another substance, such as GFP (green fluorescent protein), a LED emitting a wavelength of about 400-500 nm would be suitable, and for yet other substances other wavelengths would be used. A second additional filter 18 may be arranged to allow light of a small wavelength range, preferably only 10 nm, to pass through before entering the third conductor 6 and being transmitted to the flow cell 2. In some embodiments, especially if the second light source 4 is a laser, no second additional filter 18 will generally be required.

Light from the second light source 4 thus enters the flow cell 2 through the second inlet 12 and irradiate the sample contained therein. Fluorescence signals will thereby be generated, having a wavelength differing from the light from the second light source 4. Said fluorescence signals will be transmitted through the outlet 13 and the second conductor 7 to the sample detector 9 and through the first filter 8, and will generate a third signal 33 in the sample detector, corresponding to the magnitude of the fluorescence signals from the sample. Said third signal 33 may be transmitted to the processing unit 16 to be presented to a user and/or saved and analyzed further.

It is advantageous if the second inlet 12 and the third conductor 6 are arranged at an angle to the outlet 13 and the second conductor 7, since the amount of light directly from the second light source 4 that passes through the outlet 13 will be smaller than if the inlet and outlet are arranged facing each other. Preferably, the angle is 30°-150°, more preferably about 90°.

As mentioned above, by using a UV LED as the second light source 4, the apparatus 1 can detect native fluorescence in some substances, such as proteins and antibodies. Other compounds have native fluorescence in other ranges, for example the visible range of 400-700 nm or a higher wavelength. If desired, a fluorescence molecule or label can be bound covalently to the sample and be detected by using a second light source 4 that emits light of a wavelength corresponding to the molecule chosen. According to an embodiment of the invention, the second light source 4 can thus be replaced with different kinds of lasers or LEDs, and the first filter 8 that is arranged to prevent light of the wavelength emitted by the second light source 4 from reaching the sample detector 9 can also be changed correspondingly. In this embodiment, the second light source 4 and the first filter 8 can be removed and replaced by a user on site without changing other properties of the apparatus 1. Thus, the second light source can be replaced with a third light source and the first filter 8 with a second filter, said second filter being a band pass filter that is arranged to block light of the wavelength emitted by the third light source. A plurality of light sources and filters that are compatible with the apparatus 1 can be provided to allow the user to choose those most suitable for a specific application. These can then be mounted in the apparatus 1 and be used for subsequent fluorescence measurements. Alternatively, a plurality of filters and light sources can be provided in the apparatus 1 itself, and the user can switch between them by turning a wheel or engaging a switch, for instance, so that a specific light source with corresponding filter is engaged. If a second additional filter is used to allow only a narrow wavelength range from the second light source to pass, this filter is also replaceable. Yet another alternative would be to use a tunable bandpass filter that is arranged to block different wavelengths at different angles towards the incident light. In this event, the tunable bandpass filter can be controlled by software to determine which wavelengths to block, and this is also to be encompassed by the term "replaceable".

Preferably, the first and the second light source 3, 4 are pulsed, for instance by using square waves, to ensure that only the light of one of the light sources reaches the sample detector 9 at a given time. Thereby, the absorbance and the fluorescence can be measured separately, increasing the sensitivity and accuracy of the measurements without requiring any one of the light sources to be switched off completely. Another wave form, such as a sinus wave, could alternatively also be employed and be modelled by the processing unit 16 in order to extract the signals. If desired, the pulses can also be designed to allow the background light to be measured, providing reference values for the processing unit.

In one embodiment, the sample detector 9 can comprise a plurality of photo diodes, each being arranged to detect a number of wavelengths. Thereby, light of several wavelengths can be detected.

In most embodiments, the absorbance and the fluorescence are not measured simultaneously, but rather one at a time, either by pulsing the light from the first and second light sources 3, 4, or by using a shutter element 10 as shown by FIG. 1. The most suitable embodiment of the invention for use with the shutter is an alternative version of the first embodiment of FIG. 1, where the second light source 4 is mounted adjacent to the first light source 3, so that light from both light sources is allowed to enter the apparatus 1 through the first conductor 5. The third conductor 6 then serves to allow the fluorescence signals to leave the flow cell 2, and a fourth conductor (not shown) is connected to the third conductor 6 for transmitting the light to the sample detector 9. Thus, the third conductor 6 is arranged for transmitting light from the flow cell 2 to the sample detector 9. At the same time, the shutter 10 is closed to prevent light from the first light source 3 to reach the first filter 8 and the sample detector 9. Thereby, the sensitivity of the fluorescence measurements can be increased and the disturbance of additional light from the first light source 3 can largely be prevented.

It is to be understood that the apparatus 1 can also comprise additional components that serve to enhance and improve the signals being generated and the light being emitted from the first and second light source 3, 4. This is well known in the art and will not be described in detail herein. It is also to be readily understood by the person skilled in the art that the various components of the apparatus 1 can be connected to power supplies and to electrical components and circuitry that serve to enable and facilitate their normal operation, and that all signals generated by the detectors 9, 15 can be processed, analyzed, saved and presented by the processing unit.

The invention is not to be seen as limited by the specific embodiments described herein, but can be varied within the scope of the appended claims, as will be readily understood by the person skilled in the art. It would for instance be possible to perform the invention without the first filter and without the beam splitter and reference detector. It is to be noted that the features of the various embodiments described above can also generally be used in the other embodiments.

The invention claimed is:

1. Apparatus for measuring the fluorescence and light absorbance of a sample, said apparatus comprising
   a flow cell for containing a sample,
   a first light source,
   a first light path allowing the propagation of light from the first light source into the flow cell for irradiating a sample contained therein,
   a second light path allowing that portion of the irradiating light which is not absorbed by the sample in the flow cell to propagate to a sample detector arranged to determine the amplitude of said portion of the irradiating light, and said apparatus further comprising
   a second light source, and
   a third light path allowing the propagation of light from the second light source into the flow cell to further irradiate the sample,
   and wherein the sample detector is further arranged to detect any light resulting from the fluorescence of said sample as a result of said further irradiance.

2. The apparatus of claim 1, wherein one or more of said light paths is in the form of a light conductor, for example an optical fiber.

3. The apparatus of claim 2, further comprising
   a beam splitter connected to the first light source for receiving light and splitting it into a first portion and a second portion, wherein the first conductor is arranged to receive the second portion,
   a reference detector arranged to receive the first portion of light and detect electromagnetic radiation therein, and
   a processing unit arranged to receive a first signal 31 from the reference detector and a second signal from the sample detector and to determine an absorbance based on said first and second signals.

4. The apparatus of claim 1, wherein said sample detector is at least one photo detector.

5. The apparatus of claim 1, wherein said first light source is an UV light emitting diode.

6. The apparatus of claim 1, wherein said second light source is an UV light emitting diode.

7. The apparatus of claim 1, wherein the first light source and the second light source are pulsed.

8. The apparatus of claim 1, wherein a first filter is arranged between the second conductor and the sample detector, said first filter being a band pass filter that is arranged to block light of the wavelength emitted by the second light source.

9. The apparatus of claim 1, wherein the first conductor is also the third conductor so that light from the first light source and the second light source are transmitted through the same conductor to the flow cell.

10. The apparatus of claim 1, wherein the third conductor is arranged at an angle to the second conductor.

11. The apparatus of claim 9, wherein said angle is 30°-150°, preferably about 90°.

12. The apparatus of claim 1, wherein the second conductor comprises a shutter element for preventing light from emitting from said first inlet.

13. The apparatus of claim 12, wherein the third conductor is arranged for transmitting light from the flow cell to the sample detector.

14. The apparatus of claim 1, wherein the second light source and the first filter are arranged to be replaceable by a user of the apparatus.

15. A method for measuring the absorbance and the fluorescence of a substance in a sample, said method comprising
   providing a flow cell for containing a sample,
   transmitting light from a first light source to the flow cell for irradiating a sample contained therein,
   transmitting light from the flow cell to a sample detector for quantifying an electromagnetic radiation and obtain a sample value for determining an absorbance of the sample in the flow cell,
   and said method further comprising
   transmitting light from a second light source to the flow cell for irradiating the sample contained therein,
   transmitting light from the flow cell to the sample detector, and
   detecting fluorescence signals with the sample detector to determine the fluorescence of the substance in the sample.

16. Method according to claim 15, further comprising
   transmitting light from the first light source through a beam splitter and diverting a first portion of the light to a reference detector for quantifying an electromagnetic radiation in said first portion of light to obtain a reference value, and determining an absorbance from said sample value and said reference value.

17. Method of claim 15, further comprising transmitting light from the cell to the sample detector through a first filter that prevents light of a wavelength emitted by the second light source from reaching the sample detector.

18. Method of claim 15, further comprising pulsing the first and the second light source.

19. Method of claim 15, further comprising transmitting light from the second light source to the flow cell through a third conductor and transmitting light from the flow cell to the sample detector through a second conductor, said inlet and outlet being at an angle to each other.

20. Method according to claim 19, wherein said angle is 30°-150°, preferably about 90°.

21. Method of claim 15, further comprising preventing the light from the first light source from reaching the flow cell.

22. Method of claim 15, further comprising removing the second light source and replacing it with a third light source, and removing the first filter and replacing it with a second filter, wherein the second filter prevents light of a wavelength emitted by the third light source from reaching the sample detector.

23. Apparatus for detecting fluorescence of a substance in a sample, said apparatus comprising a fluorescing light source and a further light source, a sample cell, a light detector, a first light path, for example a light conductor for transmitting light from said light source to the flow cell to irradiate a sample containable therein, a second light path comprising a light conductor for transmitting light from the sample cell to the light detector, and a filter arranged between the sample cell and the sample detector, said filter being arranged to prevent light emitted from the further light source from reaching the light detector, wherein the fluorescing light source and the filter are arranged to be exchangeable as a pair by a user.

* * * * *